United States Patent [19]

Grassi et al.

[11] Patent Number: 5,047,330
[45] Date of Patent: Sep. 10, 1991

[54] **COMPOUND LABELLED BY THE ACETYL CHOLINESTERASE OF *ELECTROPHORUS ELECTRICUS*, ITS PREPARATION PROCESS AND ITS USE AS A TRACER OR MARKER IN ENZYMOIMMUNOLOGICAL DETERMINATIONS**

[75] Inventors: Jacques Grassi, Charenton le Pont; Philippe Pradelles, Longjumeau, both of France

[73] Assignee: Commissariat a l'Energie Atomique, Paris, France

[21] Appl. No.: 142,247

[22] Filed: Jan. 6, 1988

Related U.S. Application Data

[63] Continuation of Ser. No. 636,613, Aug. 1, 1984, abandoned.

[30] Foreign Application Priority Data

Aug. 17, 1983 [FR] France ............................... 83 13389

[51] Int. Cl.$^5$ .............................................. C12Q 1/46
[52] U.S. Cl. ....................................... 435/20; 435/7.9; 435/19; 435/197; 435/7.92
[58] Field of Search ..................................... 435/19, 20

[56] References Cited

U.S. PATENT DOCUMENTS

| Re. 29,169 | 4/1977 | Schuurs et al. | |
|---|---|---|---|
| Re. 31,006 | 8/1982 | Schuurs et al. | |
| 3,654,090 | 7/1982 | Schuurs et al. | |
| 3,791,932 | 2/1974 | Schuurs et al. | |
| 3,850,752 | 11/1974 | Schuurs et al. | |
| 4,152,411 | 5/1979 | Schall, Jr. | 436/545 |
| 4,411,989 | 10/1983 | Grow | 435/23 X |
| 4,472,498 | 9/1984 | Masuda et al. | 436/500 X |

FOREIGN PATENT DOCUMENTS 0037110 10/1981 European Pat. Off. .
2090598 7/1982 United Kingdom .

OTHER PUBLICATIONS

*Clinica Chimica Acta*, (1978), vol. 86, pp. 267–278, "Thermometric Enzyme Linked Immunosorbent Assay in Continuous Flow System: . . . ", Carl Borrebaeck, et al.
*Clin. Chem.*, (1979), vol. 25, pp. 318–321, "An 'Antibody Electrode,' Preliminary Report on a New Approach in Enzyme Immunoassay", Jean-Louis Boitieux et al.
*Immunochemistry*, (1978), vol. 15, pp. 331–333, "Chemiluminescence Immunoassay; A New Sensitive Method for Determination of Antigens", Baruch Velan et al.
*Journal of Immunological Methods*, (1979), vol. 25, pp. 127–135, "Luminescence Immunoassay (LIA): A Solid-Phase Immunoassay Monitored . . . ", Thomas Olsson et al.
*Clinica Chimica Acta*, (1977), vol. 81, pp. 1–40, "Enzyme-Immunoassay", Schuurs et al.
*Z. Anal. Chem.*, (1976), vol. 279, pp. 206–207, "Enzymimmunoassay", M. v. d. Waart et al.
*FEBS Letters*, (1971), vol. 15, pp. 232–236, "Immunoassay Using Antigen-Enzyme Conjugates", B. K. Van Weeman et al.
*FEBS Letters*, vol. 134, No. 1, Nov. 1981, New Substrates of Acetylcholinesterase, Meira Naveh et al.
Neas-Chem. Abst. vol. 102 (1985) p. 200520f.

(List continued on next page.)

Primary Examiner—Sam Rosen
Attorney, Agent, or Firm—Oblon, Spivak, McClelland, Maier & Neustadt

[57] ABSTRACT

Compound labelled by the acetyl cholinesterase of *Electrophorus electricus*, its preparation process and its use in enzymoimmunology.

This compound is constituted by a molecule chosen from among the antigens, haptens and antibodies, bonded by a covalent bond to an enzyme formed by the acetyl cholinesterase of *Electrophorus electricus* (electric eel).

For example, the molecule is the substance P or a prostaglandin and the compound can be used for the enzymoimmunological determination of these molecules.

21 Claims, 1 Drawing Sheet

OTHER PUBLICATIONS

Masuda et al–Chem. Abst. vol. 98 (1983) p. 175837d.
Naveh et al–Chem. Abst. vol. 96 (1982) p. 99966m.
*J. Clin. Chem. Clin. Biochem.*, (1980), vol. 18, pp. 197–208, "Enzyme Immunoassays in Clinical Chemistry: Present Status and Trends", M. Oellerich.
Chem. Abs. 94:117377k (1981).
Chem. Abs. 100:168624p (1984).
Colowick et al., *Methods in Enzymology*, vol. I, Academic Press, N.Y., 1955, pp. 644–647.
Rosenberry et al., Biochemistry, vol. 16, No. 17, 3870–3878, 1977.
Bonn et al., Ann. Rev. Neurosci., vol. 5, pp. 57–106, 1982.
Chemical Abstracts, vol. 97, No. 25, Dec. 20, 1982, p. 121, No. 208627v, Yoko et al: "Enzyme Immunoassay of $PGF_{2\alpha}$".

COMPOUND LABELLED BY THE ACETYL CHOLINESTERASE OF *ELECTROPHORUS ELECTRICUS*, ITS PREPARATION PROCESS AND ITS USE AS A TRACER OR MARKER IN ENZYMOIMMUNOLOGICAL DETERMINATIONS

This application is a continuation of application Ser. No. 06/636,613, filed on Aug. 1, 1984, now abandoned.

BACKGROUND OF THE INVENTION

1. Field of the Invention

The present invention relates to a compound labelled by an enzyme, its preparation process and its use as a tracer or marker in enzymoimmunological determinations, e.g. in the form of a labelled antigen, labelled hapten or labelled antibody.

2. Discussion of the Background

It is known that in a higher vertebrate, an antigen can induce the production of specific antibodies able to form a reversible complex having a high bonding energy with the antigen. Haptens are low molecular weight substances, which do not bring about the formation of antibodies when injected into an animal, but which instead react with the antibodies. These antibodies directed against haptens can be produced on injecting into an animal or man a conjugate compound, e.g. of hapten and a protein.

The antigen—antibody or hapten—antibody reactions can be used for measuring the concentrations of haptens, antigens or antibodies in a given medium using immunoanalytical methods, such as enzymoimmunological methods. In the latter case, the reaction involves an antibody, an antigen or a hapten and a molecule labelled by an enzyme, which can either be an antigen, or the antibody, or the hapten.

As a function of the nature of the molecule labelled by the enzyme, a distinction is made between two types of immunological determination. When the labelled molecule is the antigen or hapten, reference is made to "determination by competition" or "determination in a limited reagent quantity". In this case, the principle of the determination is based on the competition between the labelled hapten or antigen on the one hand and the antigen or hapten on the other with respect to a limited number of antibody sites. Thus, for immunological determination, it is necessary to establish a calibration curve by reacting constant quantities of antibodies and labelled molecules of antigen or hapten in limiting quantities with variable hapten or antigen quantities. After establishing the antigen - antibody equilibrium, a fractionation method is used on the mixture, which makes it possible to separate the labelled complex from the antigen or hapten remaining free in solution and by measuring the enzymatic activity of the bonded fraction (complex) or the free fraction (labelled hapten or antigen), it is possible to determine the activity corresponding to the different antigen or hapten concentrations and plot the calibration curve. Once this curve has been plotted, it is possible to determine the antigen or hapten concentration of a sample by applying the same procedure and by referring to the calibration curve to obtain the hapten or antigen concentration corresponding to the enzymatic activity found during the determination.

When the labelled molecule is the antibody, reference is made to "immunometric" methods or to determination "with reagent excess". There are several variants to these methods and the three most important of these are described below.

I. "CONVENTIONAL" IMMUNOMETRIC DETERMINATION

This type of determination is known as immunoradiometric determination (IRMA) when it uses a radioactively labelled antibody.

First Stage

Reaction of the antigen with an iodized antibody excess

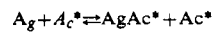

Second stage

Adsorption of the antibody excess by an antigen fixed to the solid phase (antigen excess)

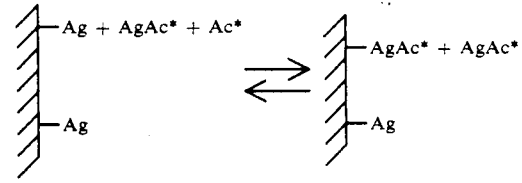

Third stage

Separation of the two phases and counting the supernatant product.

II. IMMUNOMETRIC DETERMINATION WITH TWO SITES (SANDWICH METHOD)

First stage

Reaction of the antigen with a first antibody adsorbed on the solid phase (antibody excess)

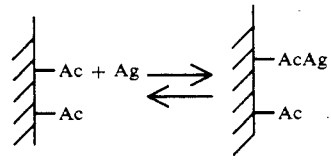

Second stage

Addition of a labelled antibody recognizing another site of the antigen (excess antibody)

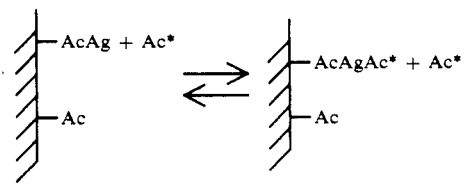

Third stage

Elimination of the labelled antibody excess by washing and counting the slid phase.

III. DETERMINATION OF THE SPECIFIC ANTIBODY USING AN IMMOBILIZED ANTIGEN

This type of determination, as well as immunometric determination with two sites are known as the ELISA method (Enzymo-Linked-Immuno-Sorbent-Assay) when using an enzymatic tracer.

First stage

Reaction of the specific antibody with the immobilized antigen (antigen excess).

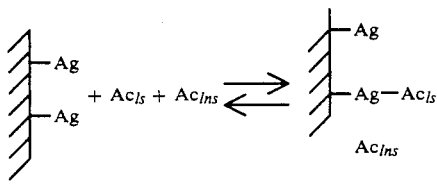

Second stage

Reaction of the double labelled antibody or the labelled protein A) with the antibody fixed to the solid phase.

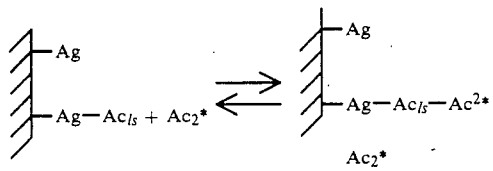

Third stage

Elimination of the excess of the double labelled antibody by washing and counting the solid phase.

Ag: antigen
$Ac_{Is}$: first specific antibody of the antigen
$Ac_{Ins}$: first non-specific antibody of the antigen
$Ac_2^*$: second labelled antibody.

They all have the following characteristics in common:
- the antibody is labelled either directly, or by means of another labelled molecule with which it can react and these specific reagents of the antibody can be "second antibodies" or the protein A of "Staphylococcus aureus";
- one of the reactants, which can either be the antibody or the antigen or hapten is fixed to the solid phase, so as to separate the antibody which has reacted from that which has remained free in solution (cf determinations I, II and III);
- one or more of the reactants, which can either be the antibody or the antigen or hapten is in considerable excess compared with one or more other reactants and it is for this reason that these methods are called "reagent excess" methods.

In addition to the classification given hereinbefore, among the enzymoimmunological determinations a distinction is made between two determination types, namely "homogeneous" and "heterogeneous" determinations. A homogeneous determination is based on the fact that the activity of the labelled molecule is modified when it is bonded to the corresponding antibody or antigen. In this case, the enzymatic activity of the reaction mixture is directly linked with the proportion of labelled molecules involved in the formation of the antigen - antibody complex. Therefore, there is no need to carry out a separation and the measurement of the enzymatic activity can take place directly in the reaction media.

However, in a "heterogeneous" enzymoimmunological determination, it is necessary to use a separation process, because in this case the enzymatic activity of the molecule labelled by the enzyme which has participated in the formation of the complex is not modified. In this case, it is necessary to separate the antigen-antibody complex from the reaction medium in order to measure the enzymatic activity of the complex, or of the free antigen or antibody. Most hitherto developed enzymoimmunological determinations belong to this category.

The enzyme used plays a very important part in all these determinations, because it conditions the performances of the determinations and the enzymes able to satisfy the following requirements are sought:

1) Availability of large quantities of the enzyme in the pure state, so that the labelled antigen, hapten or antibody molecules can be produced under good conditions.
2) Possibility of a highly sensitive detection of the enzyme, so that it is possible to measure very small quantities of the antigen - antibody complex and consequently very small quantities of antigen, hapten or antibody in the samples. This detection sensitivity is obviously dependent on the catalytic constant of the enzyme, but also on the sensitivity with which it is possible to measure the products of the enzymatic reactions.
3) Very simple enzymatic determination.
4) Presence in the enzyme of reactive groups able to react with the antigens, haptens or antibodies to form the labelled molecule.
5) Stability of the enzyme in standard conservation conditions.
6) Enzymatic activity of the enzyme not identical to that of the determination medium and not having factors interfering with the determination.
7) Minimum autolysis of the enzymatic substrate.

SUMMARY OF THE INVENTION

The research carried out has revealed that the acetyl cholinesterase of *Electrophorus electricus* or electric eel forms an enzyme having optimum characteristics for use in an immunoenzymatic determination and the present invention specifically relates to the use of this enzyme for preparing compounds usable as labelled molecules in an immunoenzymatic determination.

The compound according to the invention is constituted by a molecule chosen from among the antibodies, the antigens and the haptens, bonded by a covalent or reversible bond to an enzyme and is characterized in that the enzyme is constituted by the acetyl cholinesterase of *Electrophorus electricus* or the electric eel.

DETAILED DESCRIPTION OF THE PREFERRED EMBODIMENTS

Figure 1:
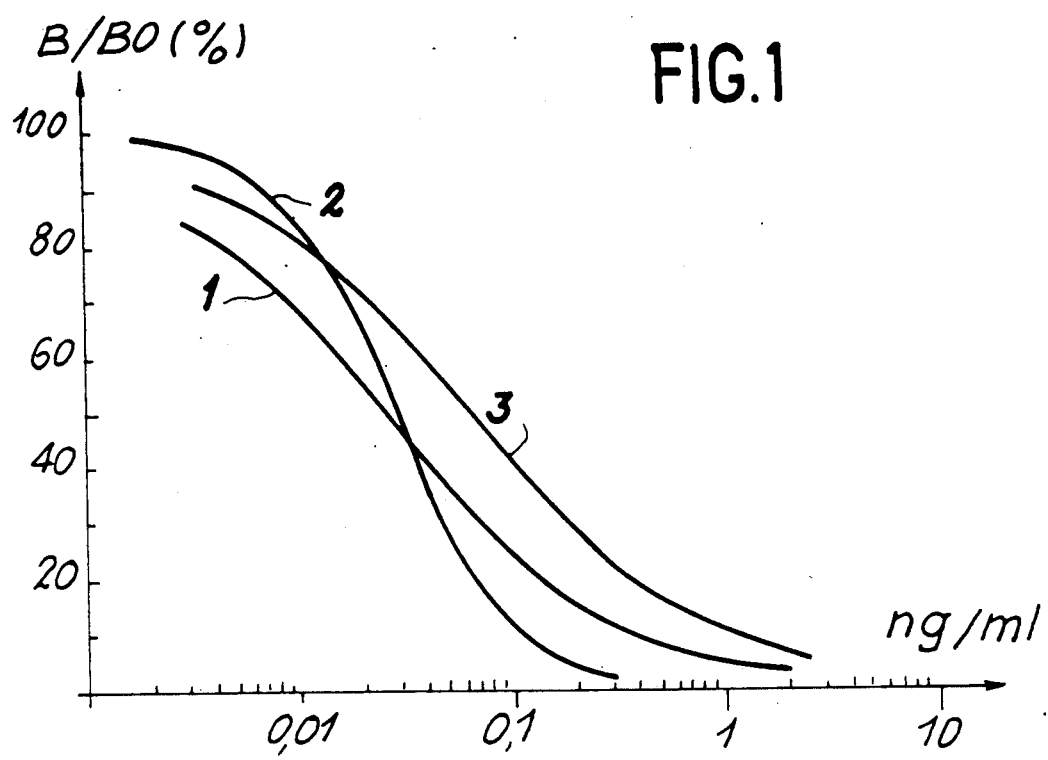

As a result of the use of this enzyme, it is possible to carry out enzymoimmunological determinations under good conditions.

Acetyl cholinesterase (E.C.3.1.1.7) forms part of a group of enzymes, which rapidly hydrolyze the esters of choline and is characterized in that acetyl choline is its best substrate. It is very widely distributed in numerous animal tissues and in the central and peripheral nervous system of vertebrates. It is found in a particularly large concentration in the electric organs of certain fish, such as *Electrophorus electricus* and Torpédo Marmorata. Acetyl cholinesterase is concentrated 100 times more in the electric organs of the electric eel than in the brain of birds or mammals. The enzyme contained in the electric organs of the electric eel is rapidly and simply purified in one stage by affinity chromatography. Its purification can be performed much more easily than that of the acetyl cholinesterase of Torpédo Marmorata, birds or animals, which all at least partly have hydrophobic characteristics and reduced stability.

Electric eel acetyl cholinesterase also has a very high catalytic constant and can be detected by colorimetric determination up to concentrations of approximately $10^{-13}M$. This detection sensitivity is significantly higher than that which can be observed with the main enzyme used in enzymoimmunology, namely Raifort peroxidase (E.C.1.11.1.7), Escherichia Coli $\beta$-galactosidase (E.C.3.2.1.23) and the alkaline phosphatase of calf intestine (E.C.3.1.3.1).

Moreover, it also has reactive groups, such as lysyl, tyrosyl, histidyl, tryptophanyl and glutamyl groups, which can react with certain reactive groups of antigens, haptens or antibodies to form labelled compounds usable in enzymology. Finally, this enzyme is very stable at $-20°$ C. or at $-173°$ C., provided that it is preserved in a suitable medium.

Therefore, numerous advantages result from the use of electric eel acetyl cholinesterase as an enzymatic tracer, both compared with other acetyl cholinesterases and compared with other enzymes presently used in the field of enzymoimmunology.

According to the invention, electric eel acetyl cholinesterase (EC3.1.1.7) is obtained from the electric organs of the electric eel, purified by affinity chromatography. In particular, it is possible to use the method described by Bon et al in Eur. J. Biochemical 68, pp.531–539, 1976, which makes it possible to obtain approximately 30mg of pure enzyme in a few days from one kilogram of electric organ of the electric eel.

It is known that acetyl cholinesterase exists in several molecular forms called $A_{12}$, $A_8$, $A_4$, $G_4$, $G_2$ and $G_1$, as described by Bon et al in Ann. Rev. Neurosci., 1982, 5, pp.57–106. The forms $A_{12}$, $A_8$ and $G_4$ predominate in the electric organs of the electric eel and when the pure enzyme is stored covalent aggregates between the $A_{12}$ and $A_8$ forms can spontaneously form.

According to the invention, the compound can be formed from the natural molecular forms such as $A_{12}$, $A_8$ and $G_4$, but also from molecular forms obtained by degradation of the latter, namely $A_4$, $G_2$ and $G_1$, or even from covalent aggregates between the asymmetrical forms.

According to the invention, the molecule constituted by an antigen or a hapten can be chosen from among the medicaments such as analgesics, antibiotics, anticonvulsants, antidiabetic agents, antihypertensive agents, antineoplastic agents, barbiturates, cardiac depressants, cardiac glycosides, hallucinogens, insecticides, muscle relaxants, steroids, stimulants, tobacco alkaloids and tranquilizers. This molecule can also be constituted by a protein of the plasma or a hormone, e.g. a polypeptide, a steroid or other smaller molecules.

For example, the antigens can be serum proteins such as IgG, IgE, haptoglobin, alpha-2-H-globulin, alpha-FP, CEA and PAM, the hormones can be HCG, HPL, TSH, insulin, estrogens, progesterone, cortisol and thyroxine and the medicaments can be barbiturates, opiates, methadone, amphetamines, digoxin and gentamicin.

The molecule can also be formed by antibodies of certain pathogens such as *Echinococcosis granulosus, Trichinella Spiralis, Toxoplasma gondii, Treponema pallidum*, the Salmonella O antigens, *Escherichia coli*, Rubella virus, *Trypanosoma brucci, Trypanosoma cruzi, Schistosoma mansoni, Schistosoma haematobium, Plasmodium berghei, Plasmodium knowlesi and Vibrio cholerae*. It can in particular be formed by a monoclonal antibody.

For example, we will refer to results obtained with the following molecules: substance P, prostaglandins, thromboxan, leucotrien, triiodothyronine (T3), human anti-IgE antibody.

According to the invention, for bonding by a covalent bond, electric eel acetyl cholinesterase to the molecule chosen from among the antigens, haptens and antibodies, one of the reactive groups carried by the enzyme such as the lysyl, tyrosyl, histidyl, tryptophanyl or glutamyl groups is reacted with a reactive group carried by the antigen, hapten or antibodies, e.g. with an acid function, amine function, phenol function, hydroxyl function or ketone function. This can be more particularly carried out by the currently used coupling reactions, by means of reagents such as carbodiimides, glutaraldehyde, benzidine, mixed anhydrides, active hapten esters and paraaminophenyl acetic acid.

According to the invention, the bond between the antigen, hapten or antibody can also be obtained by means of a non-covalent, reversible bond, like that of avidin and biotin, or an antigen and an antibody.

Thus, the process of the invention consists of reacting the molecule chosen from among the antigens, haptens and antibodies with the electric eel acetyl cholinesterase.

According to a particular embodiment of this process, when the molecule is substance P, a derivative thereof is firstly prepared by reacting it with an active ester or paraaminophenyl acetic acid and the thus obtained derivative is reacted with electric eel acetyl cholinesterase.

According to another embodiment of the process according to the invention, when the molecule is a prostaglandin, a thromboxan or triiodothyronine, an active ester of prostaglandin is firstly prepared and the thus obtained ester is reacted with electric eel acetyl cholinesterase.

Advantageously, the active ester is obtained by reacting the free acid of the molecule with N-hydroxysuccinimide.

When the molecule is a leucotriene, an intermediate compound is firstly prepared by reacting the molecule with dinitrofluorobenzene before reacting it with the electric eel acetyl cholinesterase.

When the molecule is an antibody, e.g. a human anti-IgE antibody, biotin is firstly covalently fixed to the antibody and to the electric eel acetyl cholinesterase using an active ester of biotin.

The bond between the antibody and the enzyme is provided by avidin, which forms a very stable complex with the molecules of biotin.

The compounds according to the invention can be more particularly used as markers or tracers in enzymoimmunological determination processes for determining the antigen, antibody or hapten concentration of a sample, using either the "homogeneous" or "heterogeneous" determination method.

When using the heterogeneous determination method, the separation between the bonded fraction and the free fraction of the enzyme-labelled molecule is brought about by conventional methods, e.g. precipitation with the aid of a second antibody. It is also possible to use solid phases constituted by a support, to which is fixed an antigen or an antibody. In such determinations, the enzymatic activity of the acetyl cholinesterase can be determined by a conventional method, particularly that described by Ellman et al in Biochemical Pharmacology 1961, Vol. 7, pp.88-95, whose performance is particularly simple and which makes it possible to detect enzyme concentrations of approximately $10^{-13}M$.

Figure 2:
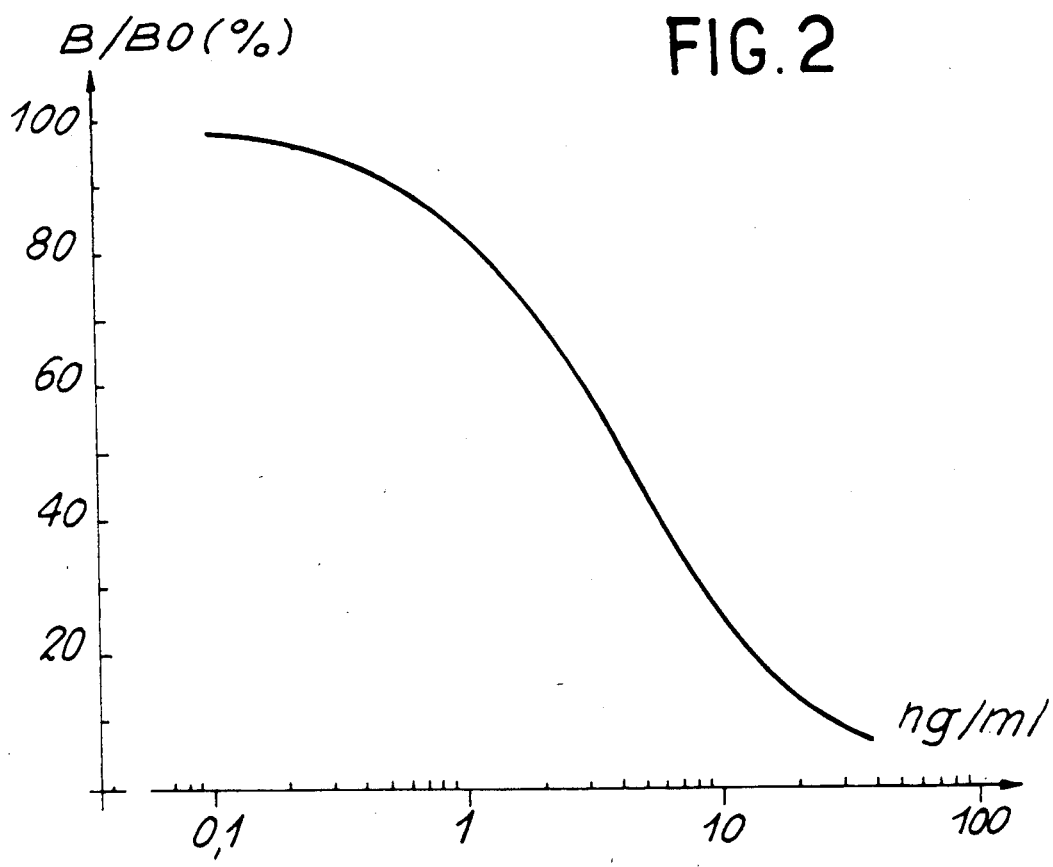

Other features and advantages of the invention can be gathered from studying the following examples given in an illustrative and non-limitative manner with reference to FIGS. 1 and 2, which show the calibration curves of enzymoimmunological determinations according to the invention.

EXAMPLE 1:

Preparation of an enzymatic tracer for the immunoenzymatic determination of substance P (SP)

This substance corresponds to the following sequence of amino acids:

Arg-Pro-Lys-Pro-Gln-Gln-Phe-Phe-Gly-Leu-Met-NH$_2$.

In order to prepare the covalent compound between substance P and electric eel acetyl cholinesterase, two stages are used consisting respectively of preparing an intermediate derivative of substance P by combination with paraaminoacetic acid (PAPA) and coupling the thus obtained derivative with the enzyme by means of a diazonium salt.

a) Preparation of the intermediate derivative of substance P

Firstly, an active ester of paraaminophenyl acetic acid (PAPA) is prepared with N-hydroxysuccinimide (NHS) according to the following reaction diagram:

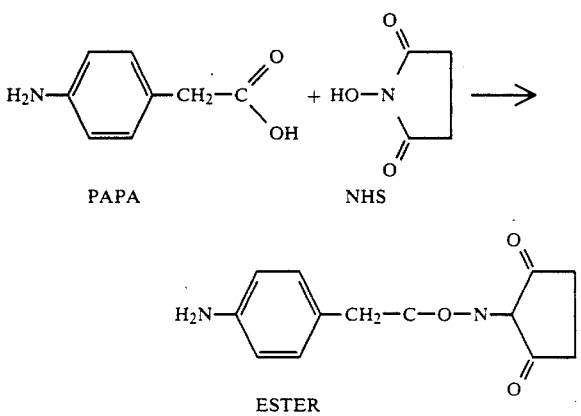

This derivative is then reacted with substance P according to the following diagram:

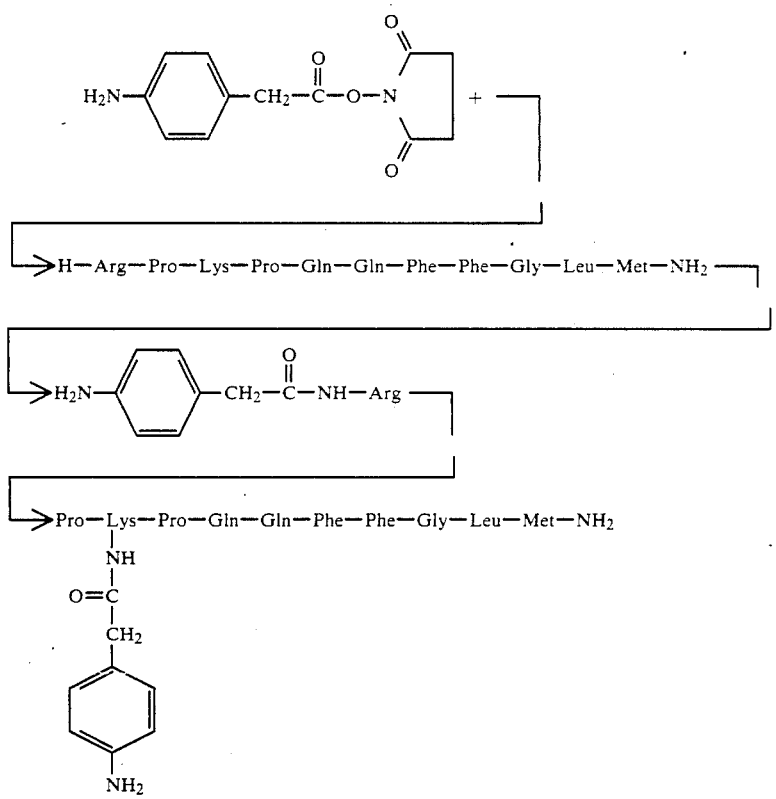

In order to prepare the active ester, 15.1 mg of PAPA, 11.5mg of NHS and 20.6mg of dicyclocarbodiimide (DCC) are reacted in 2ml of dimethylformamide (DMF) for 18 hours at 22° C. in the dark. The precipitate formed is then eliminated by centrifuging and then 20 μl (1 μmol) of the thus obtained reaction mixture is added to 100 μl of 0.1M pH 9 borate buffer/DMF (.vol/vol) containing 1 μmol of substance P (SP) and reaction is allowed to take place for 1 hour at 4° C. in the dark leading to the intermediate derivative.

b) Coupling the SP-PAPA conjugate to the enzyme

This coupling reaction corresponds to the following diagram:

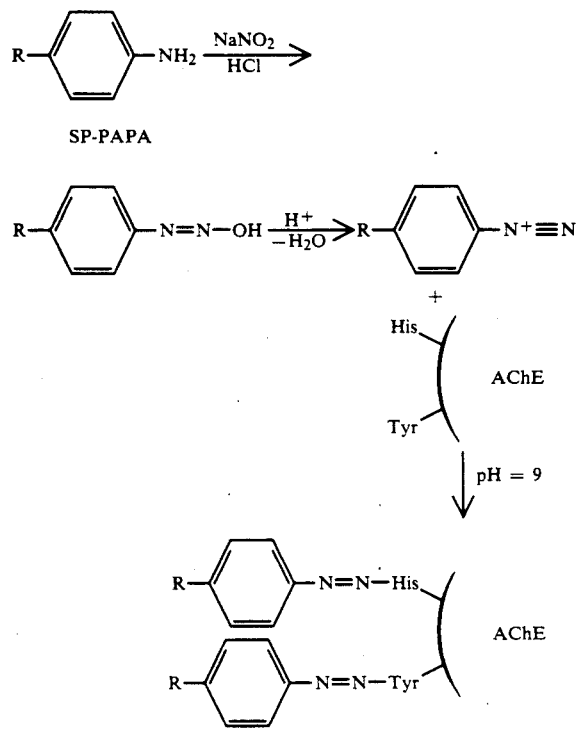

50 μl of an aqueous 0.5% NaNO solution are added to 100 μl of 1N HCl containing approximately 130 pmol of the previously obtained SP-PAPA, whilst working at 4° C. After 1 minute, this solution is added to 1ml of an enzyme solution (100 μg) in a 0.5M (pH 9) carbonate buffer. Reaction is allowed to proceed for 30 minutes at +4° C. in the dark. The excess SP-PAPA reagent not coupled to the enzyme is neutralized by adding 100 μl of histidine (100 μg) in the carbonate buffer. 15 minutes later, the reaction mixture is filtered through a (G25) Sephadex column of 2×40 cm, successively using as the eluent TRIS $10^{-2}$M buffer, MgCl$_2$ $5.10^{-2}$M and 1M NaCl (pH 7.4).

The object of this operation is to eliminate the substance P not coupled to the enzyme.

The enzymatic activity of the different collected fractions is then measured and in this way the elution profile of the enzymatic activity is determined. The fractions are combined, then distributed into several freezing tubes, and are preserved in liquid nitrogen. Gel filtration is then used to purify the compounds corresponding to the different enzyme forms (aggregate forms $A_8$–$A_{12}$ and $G_4$) using A15m gel (Biorad) in a 90×1.5 cm column and whilst using the aforementioned TRIS buffer as the eluent. After obtaining the elution profile of the enzymatic activity, the different fractions of the peak are combined, these corresponding to the elution of the different forms. The enzymatic tracer is stored in liquid nitrogen until it is used.

EXAMPLE 2:

Preparation of an enzymatic process for the immunoenzymatic determination of 6-keto-PGF$_{1\alpha}$, which is a prostacyclin metabolite 6-keto-PGF$_{1\alpha}$ corresponds to the following formula:

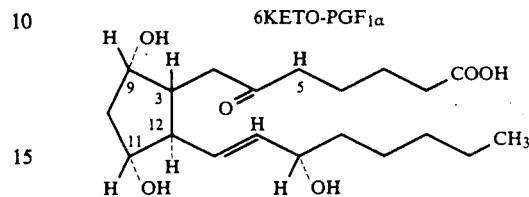

The compound is obtained in two stages consisting respectively of forming an active ester of 6-keto-PGF$_{1\alpha}$ and then coupling the active ester to the enzyme.

a) Preparation of the active ester

10 μl of DMF containing 5.1 μmol of N-hydroxysuccinimide (NHS) and 10 μl of DMF containing 5.1 μmol of dicyclocarbodiimide (DCC) are added to 100 μl of anhydrous DMF containing 5.1 μmol of 6-keto-PGF$_{1\alpha}$ and reaction is allowed to take place for 18 hours at 22° C. in the dark, which leads to the formation of the active ester of 6-keto-PGF$_{1\alpha}$, in accordance with the following reaction diagram:

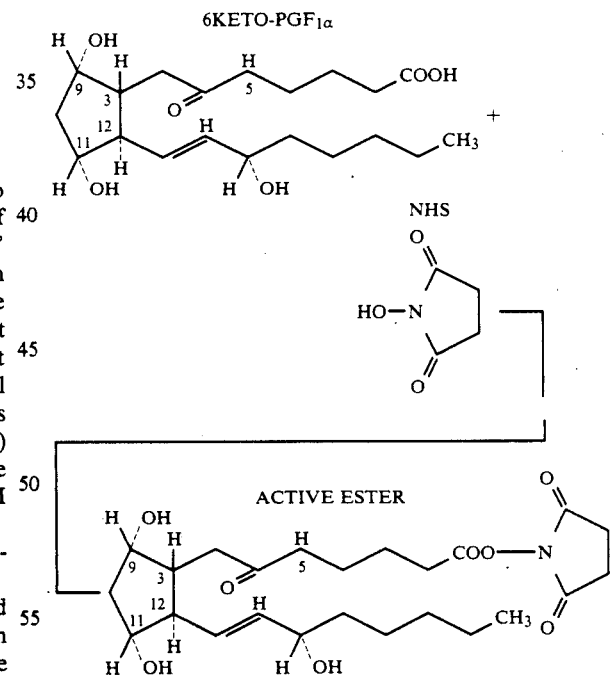

b) Coupling of the 6-keto-PGF$_{1\alpha}$ to the enzyme.

2 μl of the active ester solution in 50 x diluted DMF obtained in stage a), (i.e. approximately 10 mmol of active ester are added to 500 μl of 0.1M (pH 9) borate buffer containing 250 μl of acetyl cholinesterase. The reaction is allowed to continue for 1 hour at +4° C. and the ester excess is neutralized by adding 1 ml of 0.M phosphate buffer 0.4M NaCl, $10^{-3}$M ethylenediaminotetraacetic acid and 0.5% BSA. This leads to the coupling of the enzyme in accordance with the following reaction diagram:

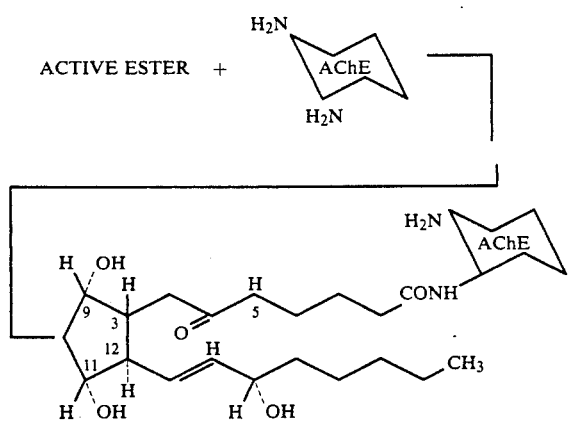

This is followed by the purification of the compounds corresponding to the different forms of the enzyme by gel filtration in accordance with the method described in example 1.

EXAMPLES 3, 4 and 5

The procedure of example 2 is adopted for preparing $PGD_2$-MO, thromboxan B2 and triiodothyronine labelled by electric eel acetyl cholinesterase and using the same synthesis methods.

EXAMPLE 6

Preparation of an enzymatic tracer for the immunoenzymatic determination of leucotriens, e.g. leucotrien $C_4$. Leucotrien $C_4$ ($LTC_4$) corresponds to the following formula:

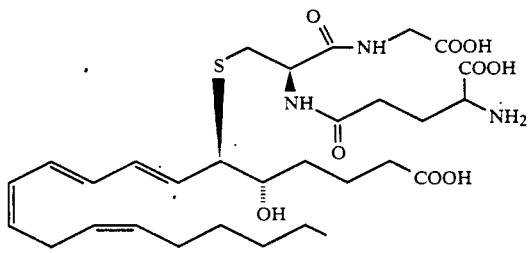

The compound is produced in two stages consisting respectively of forming an active derivative of $LTC_4$ and then coupling this derivative to the enzyme.

a) Preparation of the active derivative of $LTC_4$

To 100 μl of the phosphate buffer containing 50 μg of $LTC_4$ (0.1M, pH 7.4) are added 60 μl of methanol containing 200 μg of DFDB (difluorodinitrobenzene). The reaction is allowed to proceed for 30 minutes at 22° C. The methanol is evaporated in vacuo and the excess DFDB is extracted by 3×0.5 ml of ether. The excess ether is evaporated in nitrogen.

b) Coupling the $LTC_4$ to the enzyme

60 μl of the previously obtained reagent are added to 250 μl of borate buffer (0.1M, pH 9) containing approximately 100 μg of enzyme. After reacting for 4 hours at 22° C., 200 μl of phosphate buffer, BSA are added. The purification of the coupling products takes place according to the method described in example 1 using A15m gel filtration (Biorad).

EXAMPLE 7

Preparation of an enzymatic tracer for human IgE determination using an acetyl cholinesterase-labelled human anti-IgE antibody by means of the avidin-biotin system.

The coupling principle is based on the very strong interaction existing between avidin, which is a protein extracted from egg white and biotin, which is a vitamin. Avidin has the property of being able to fix several biotin molecules and can therefore serve as a bond between two molecules to which biotin has been previously fixed.

Biotin corresponds to the following formula:

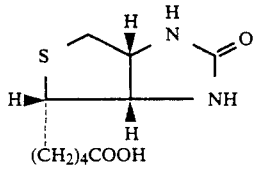

In order to covalently label the antibody and the enzyme by biotin, use is made of an active ester of the molecule. For example, it can be an ester of N-hydroxysuccinimide prepared under conditions similar to those described in example 3. The reaction of the ester with the antibody and the enzyme is also obtained in the same way as in example 2.

Coupling between the antibody and the enzyme is carried out at the time of the determination in the following way. The biotin-labelled anti-IgE antibody is reacted with human IgE previously fixed to a solid support by means of another unlabeled anti-IgE antibody. After reaction and eliminating the labelled excess antibody which has not reacted, an avidin excess is added and is fixed to the biotin-labelled antibody. After eliminating the excess avidin which has not reacted, biotin-labelled acetyl cholinesterase is added, which is fixed to the avidin molecules bonded to the labelled antibody, thus bringing about the coupling between the antibody and the enzyme.

EXAMPLE 8

This example illustrates the use of the compound obtained in example 4 for the enzymoimmunological determination of thromboxan $B_2$ ($TXB_2$).

For this test, use is made of $TXB_2$ labelled with electric eel acetyl cholinesterase forms $A_8$-$A_{12}$, a first antibody constituted by the anti-$TXB_2$ rabbit antiserum and a second antibody constituted by the rabbit anti-gamma-globulin pig antiserum. The latter antibody is fixed to a solid phase.

In order to also carry out the immunological test, the following procedure is adopted:

a) Preparation of the second fixed antibody

To each cavity or depression of an "ImmunoNune" 96F microtitration plate is added 300 μl of a rabbit anti-IgG solution purified by affinity chromatography (10 μg/ml) containing 2% glutaraldehyde in phosphate buffer ($10^{-2}$M, pH 7.4). After incubating for 12 hours at 22° C., the solution in each cavity is eliminated and 300 μl of the previously described B5A phosphate buffer are added.

b) Enzymoimmunological reaction

The content of each cavity is eliminated and to each is added 50 μl of an enzymatic tracer solution, 50 μl of an anti-TXB$_2$ antibody solution and 50 μl of the different TXB$_2$ concentrations or 50 μl of the sample to be determined.

After incubating for 12 hours at +4° C., the content of each cavity is eliminated and 200 μl of enzymatic substrate (Ellmann reagent) are added. Following enzymatic reaction lasting 1 hour at 22° C., the absorptivity at 414 nm is measured in each cavity using the multiscan TITEKTEK (Flow Laboratories) spectrophotometer. Curve 1 of FIG. 1 illustrates the calibration curve of the enzymoimmunological determination of TXB$_2$ using the compound of example 4 as the tracer and makes it possible to determine the TXB$_2$ concentration of the sample.

On the abscissa of FIG. 1 is plotted the dose (pg/cavity) of TXB$_2$ and on the ordinate the B/Bo percentage ratio in which B represents the enzymatic activity linked with the antibodies in the presence of TXB$_2$ and Bo represents the enzymatic activity linked with the antibodies in the absence of TXB$_2$. The non-specific bonding values have been subtracted and represent less than 5% of the total activity.

EXAMPLE 9

This example illustrates the use of the compound obtained in example 2 for the enzymoimmunological determination of 6-keto-PGF$_{1\alpha}$. The test protocol is the same as that described for the thromboxan in example 8. The calibration curve relating to this determination is shown in curve 2 of FIG. 1.

EXAMPLE 10

This example illustrates the use of the compound obtained in example 3 for the enzymoimmunological determination of PGD$_2$-MO. The test protocol is the same as that described in example 8. The calibration curve relating to this determination is shown in curve 3 of FIG. 1.

EXAMPLE 11

This example illustrates the use of the compound obtained in example 5 for the enzymoimmunological determination of triiodothyronine (T$_3$). The test protocol is identical to that described in example 8. The calibration curve relating to this determination is shown in FIG. 2.

What is claimed is:

1. A compound, comprising:
   (i) a molecule component which is at least one member selected from the group consisting of antigens, haptens and antibodies; and
   (ii) an enzyme component, wherein said enzyme is molecular form A$_{12}$, A$_8$ or G$_4$, or an aggregate of these forms, of acetyl cholinesterase obtained from *Electrophorus electricus*;
   wherein said molecule component and said enzyme component are bonded to each other via a covalent bond or a reversible bond, and wherein said compound is usable as an enzymoimmunologic tracer or marker.

2. A compound according to claim 1, wherein the molecule component is a prostaglandin, a thromboxan or a leucotrien.

3. A compound according to claim 2, wherein the prostaglandin is 6-keto-PGF$_{1\alpha}$ or PGD$_2$-MO.

4. A compound according to claim 2, wherein the thromboxan is thromboxan B$_2$.

5. A compound according to claim 2, wherein the leucotrien is leucotrien C$_4$.

6. A compound according to claim 1, wherein the molecule component is triiodothyronine (T$_3$).

7. A compound according to claim 1, wherein the molecule component is a human anti-IgE antibody.

8. A compound according to claim 1, wherein the molecule component is a monoclonal antibody.

9. A compound according to claim 1, wherein the molecule component is substance P.

10. The compound of claim 1, comprising:
    (i) a molecule component which is at least one member selected from the group consisting of antigens, haptens, and antibodies; and
    (ii) an enzyme, wherein said enzyme is acetyl cholinesterase obtained from *Electrophorus electricus*;
    wherein said molecule component and said enzyme are bonded to each other via a covalent bond, and wherein said compound is usable as an enzymoimmunologic tracer or marker.

11. The compound of claim 1, comprising:
    (i) a molecule component which is at least one member selected from the group consisting of antigens, haptens, and antibodies; and
    (ii) an enzyme, wherein said enzyme is acetyl cholinesterase obtained from *Electrophorus electricus*;
    wherein said molecule component and said enzyme are bonded to each other via a reversible bond, and wherein said compound is usable as an enzymoimmunologic tracer of marker.

12. The compound of claim 1, wherein said molecular form comprises G$_4$.

13. The process for the preparation of a compound comprising (i) a molecule component which is at least one member selected from the group consisting of antigens, haptens, and antibodies, and (ii) an enzyme component, wherein said enzyme is molecular form A$_{12}$, A$_8$ or G$_4$, or an aggregate of these forms, of acetyl cholinesterase obtained from *Electrophorus electricus*, said process comprising:
    (1a) reacting at least one reactive group on said molecule component with at least one reactive group of said enzyme component, wherein said enzyme is used as purified said molecular form A$_{12}$, A$_8$ or G$_4$, or as an aggregate of these forms, to obtain said compound in which said molecule component and said enzyme component are bonded to each other via a covalent bond, or (1b1) causing the formation of a non-covalent reversible bond between said molecule and said enzyme,
    wherein said enzyme is used as purified said molecular form A$_{12}$, A$_8$ or G$_4$, or as an aggregate of these forms, to obtain said compound in which said molecule component and said enzyme component are bonded to each other via a reversible bond; and
    (2) obtaining said compound in a form suitable for use as an enzymoimmunologic tracer or marker.

14. A process according to claim 13, wherein the active ester of prostaglandin is prepared by reacting prostaglandin with N-hydroxysuccinimide.

15. The process of claim 13, wherein the molecule component is substance P, comprising preparing a derivative of substance P by reacting substance P with an active ester of para-aminophenyl-acetic acid to obtain a derivative, which is then reacted with acetyl cholinesterase obtained from *Electrophorus electricus*.

16. The process of claim 13, wherein the molecule component is prostaglandin, thromboxan or triiodothyronine, comprising preparing an active ester of prostaglandin, thromboxan, or triiodothyronine, and then reacting the said active ester with acetyl cholinesterase obtained from *Electrophorus electricus*.

17. In an enzymoimmunological assay in which the presence or concentration of a hapten, an antigen or an antibody in a biological sample is determined by means of an antigen-antibody or a hapten-antibody reaction, the improvement comprising using a compound comprising:

(i) a molecule component which is at least one member selected from the group consisting of antigens, haptens, and antibodies; and (ii) an enzyme component, wherein said enzyme is molecular form $A_{12}$, $A_8$ or $G_4$, or an aggregate of these forms, of acetyl cholinesterase obtained from *Electrophorus electricus*;

wherein said molecule component and said enzyme component are bonded to each other via a covalent bond or a reversible bond, and wherein said compound is usable as an enzymoimmunologic tracer or marker.

18. In the process of claim 17, the improvement comprising using the compound in which the said molecule component is prostaglandin, a thromboxan, or a leucotrien.

19. In the process of claim 17, the improvement comprising using a compound in which the molecule component is triiodothyronine ($T_3$).

20. In the process of claim 17, the improvement comprising using the compound in which the said molecule component is a monoclonal antibody.

21. In the process of claim 17, the improvement comprising using a compound in which the said molecule component is substance P.

* * * * *